US011045366B2

(12) United States Patent
Juhasz (10) Patent No.: US 11,045,366 B2
(45) Date of Patent: Jun. 29, 2021

(54) PERSONAL VEHICLE, AND CONTROL APPARATUS AND CONTROL METHOD THEREFORE

(71) Applicant: Now Technologies Zrt., Budapest (HU)

(72) Inventor: Marton Juhasz, Budapest (HU)

(73) Assignee: Now Technologies Zrt., Budapest (HU)

( * ) Notice: Subject to any disclaimer, the term of this patent is extended or adjusted under 35 U.S.C. 154(b) by 1060 days.

(21) Appl. No.: 15/039,062

(22) PCT Filed: Dec. 5, 2014

(86) PCT No.: PCT/HU2014/000121
§ 371 (c)(1),
(2) Date: May 25, 2016

(87) PCT Pub. No.: WO2015/082947
PCT Pub. Date: Jun. 11, 2015

(65) Prior Publication Data
US 2017/0189250 A1    Jul. 6, 2017

(30) Foreign Application Priority Data
Dec. 5, 2013 (HU) .................................. P1300703

(51) Int. Cl.
*A61G 5/04* (2013.01)
*B60L 15/20* (2006.01)
(Continued)

(52) U.S. Cl.
CPC ................ *A61G 5/043* (2013.01); *A61F 4/00* (2013.01); *B60L 15/20* (2013.01); *G05D 1/0276* (2013.01);
(Continued)

(58) Field of Classification Search
CPC .. A61G 5/043; A61G 2203/14; G05D 1/0276; B60L 15/20; B60L 2240/42;
(Continued)

(56) References Cited

U.S. PATENT DOCUMENTS 5,555,495 A * 9/1996 Bell ...................... B60W 40/08
180/907
6,415,223 B1 * 7/2002 Lin ........................ G01C 21/20
340/988

(Continued)

FOREIGN PATENT DOCUMENTS

| WO | 2007082969 | 7/2007 | | |
|---|---|---|---|---|
| WO | WO-2009138089 A1 * | 11/2009 | ............... | A61F 4/00 |
| WO | WO-2011147418 A1 * | 12/2011 | ............... | A61F 4/00 |

OTHER PUBLICATIONS

Rofer et al., Controlling an Automated Wheelchair via Joystick/Head-Joystick Supported by Smart Driving Assistance, Jun. 23-26, 2009, IEEE, 11th International Conference on Rehabilitation Robotics (Year: 2009).*

(Continued)

*Primary Examiner* — Genna M Mott
(74) *Attorney, Agent, or Firm* — Wood Herron & Evans LLP (57) ABSTRACT

The invention is a control apparatus for a personal vehicle, in particular for wheelchair (10), the control apparatus comprising: a first motion sensing unit (11) adapted for being mounted on a body part and for determining orientation with respect to an external frame of reference, a second motion sensing unit (12) adapted for being mounted on the personal vehicle and for determining orientation with respect to the same external frame of reference, and a processing unit (13) adapted for outputting an inertial control signal corresponding to a relative orientation of the first motion sensing unit (11) and of the second motion sensing (Continued)

unit (12) determined on the basis of a first orientation supplied by the first motion sensing unit (11) and of a second orientation supplied by the second motion sensing unit (12). The invention is furthermore a personal vehicle provided with the control apparatus, and a control method therefore.

5 Claims, 11 Drawing Sheets (51) Int. Cl.
    *A61F 4/00*           (2006.01)
    *G05D 1/02*          (2020.01)

(52) U.S. Cl.
    CPC ....... *A61G 2203/14* (2013.01); *B60L 2200/34* (2013.01); *B60L 2240/42* (2013.01); *Y02T 10/72* (2013.01)

(58) Field of Classification Search
    CPC .... B60L 2200/34; A61F 4/00; Y02T 10/7258; Y02T 10/72
    See application file for complete search history.

(56) References Cited

U.S. PATENT DOCUMENTS

| | | | | |
|---|---|---|---|---|
| 7,337,650 | B1 * | 3/2008 | Preston | B60W 40/11 73/1.38 |
| 9,900,669 | B2 * | 2/2018 | Touma | A63B 24/0003 |
| 2003/0127261 | A1 * | 7/2003 | Borroni-Bird | B60G 3/18 180/65.1 |
| 2005/0060093 | A1 * | 3/2005 | Ford | G01C 21/165 701/472 |
| 2006/0227030 | A1 * | 10/2006 | Clifford | G08C 17/00 341/176 |
| 2007/0015611 | A1 * | 1/2007 | Noble | A61B 5/1116 473/450 |
| 2008/0048931 | A1 * | 2/2008 | Ben-Ari | A42B 3/0433 345/8 |
| 2008/0135321 | A1 * | 6/2008 | Ripple | A61G 5/043 180/282 |
| 2009/0074252 | A1 * | 3/2009 | Dariush | G11C 11/5621 382/107 |
| 2009/0254279 | A1 * | 10/2009 | Han | G01C 21/16 701/501 |
| 2010/0318257 | A1 * | 12/2010 | Kalinadhabhotla | G01P 21/00 701/31.4 |
| 2011/0046781 | A1 * | 2/2011 | Summer | B25J 9/162 700/248 |
| 2011/0257786 | A1 * | 10/2011 | Caron L'Ecuyer | A61G 5/10 700/258 |
| 2012/0053890 | A1 * | 3/2012 | Van Acht | A61B 5/1038 702/151 |
| 2012/0143400 | A1 | 6/2012 | Hinkel, III | |
| 2012/0185098 | A1 * | 7/2012 | Bosscher | B25J 5/005 700/260 |
| 2012/0245839 | A1 * | 9/2012 | Syed | G01C 21/165 701/408 |
| 2013/0046438 | A1 * | 2/2013 | Summer | A61G 5/10 701/36 |
| 2013/0090931 | A1 * | 4/2013 | Ghovanloo | G06F 3/011 704/275 |
| 2013/0253769 | A1 * | 9/2013 | Kamo | B62D 11/003 701/42 |
| 2014/0051518 | A1 * | 2/2014 | Russo | G01C 17/30 463/37 |
| 2014/0163736 | A1 * | 6/2014 | Azizian | A61B 6/102 700/259 |
| 2014/0299398 | A1 * | 10/2014 | Hinkel, III | B62D 1/00 180/167 |
| 2015/0192656 | A1 * | 7/2015 | Werner | G01S 3/46 342/352 |
| 2015/0324636 | A1 * | 11/2015 | Bentley | G11B 27/17 386/227 |
| 2016/0018902 | A1 * | 1/2016 | Nasiri | G06F 1/1694 463/38 |
| 2017/0244937 | A1 * | 8/2017 | Meier | H04N 5/23216 |

OTHER PUBLICATIONS

European Patent Office, International Search Report and Written Opinion of the International Searching Authority, dated Apr. 29, 2015.

* cited by examiner

PERSONAL VEHICLE, AND CONTROL APPARATUS AND CONTROL METHOD THEREFORE

This application claims priority, under Section 371 and/or as a continuation under Section 120, to PCT Application No. PCT/HU2014/000121, filed on Dec. 5, 2014, which claims priority to Hungarian Application No. P1300703, filed on Dec. 5, 2013.

TECHNICAL FIELD

The invention relates to a personal vehicle, in particular to an electric wheelchair, controllable by means of a body-mounted inertial motion sensor, and a control apparatus and control method for the wheelchair.

BACKGROUND ART

The control device disclosed in WO 2007/082969 A1 comprises a head-mounted wireless transmitter, a microcomputer, as well as accelerometer and gyroscope microsensors adapted for measuring the angular position of the head both in the vertical and horizontal directions. A computer or an electric wheelchair can be controlled with the measured angle data. This known solution has the problem that it applies only a single sensor module which measures the combined tilt angle of the wheelchair and the user's head, and it allows for controlling the vehicle only by tilting the head. This has the following associated disadvantages:

In a real-world urban environment the head-mounted motion sensor detects the combined motion of the vehicle and the user, and thereby noises resulting from vibrations caused by the surface unevenness of the pavement are added to the control signal of the vehicle. Due to these disturbances the control system performs unwanted driving actions on the vehicle, including sudden turns and unexpected speed changes.

In case only a single head-mounted sensor is utilised, the maximum acceleration of the vehicle cannot be utilized as in case of sudden starts and stops high accelerations are measured by the sensor due to the inertia of the head, causing an oscillation between sudden starts and stops in the motion of the wheelchair.

On downward slopes and wheelchair ramps the tilt angle of the entire driver-vehicle system is measured by the head-mounted sensor. While driving on an upward slope, the user has to tilt his or her head more and more forward to prevent the vehicle from losing speed and eventually stopping. Conversely, when driving on downward slopes, if the user does tilt his or her head backwards more and more, the wheelchair may accelerate too much.

In case the head-mounted sensor becomes displaced from some reason, the relationship between the measured orientation of the head and the vehicle control signals will not be adequate. Because also the user has to learn how to drive the chair using the controller (which is not simple to set up properly), the smallest sensor displacement can make it impossible to adequately control the vehicle. In extreme cases the sensor may even fall off the head, which may lead to completely uncontrollable movements.

In many cases paralysis affects some of the muscles of the neck, but does not affect any parts of limbs. In these cases head-mounted sensors cannot be applied.

This solution, being based on detecting the motion of the head, exclusively applies acceleration sensors for measuring the tilt angle of the head. In a non-negligible fraction of cases the user is able to tilt his or her head only to a limited extent, but may be able to rotate it easily.

The device disclosed in US 2008/0048931 A1 is adapted for targeting missiles launched from an aircraft by measuring the angular position of the pilot's head relative to the aircraft. The solution combines eye- and head tracking by infrared camera with the signals of accelerometers and gyroscopes. This known solution has the disadvantage that infrared computer vision is a resource-demanding and expensive technology, which is reliable only under well controlled circumstances—such as the environment of an aircraft cockpit. The document does not disclose the utilisation of the fused signal of multiple sensors.

The arrangement disclosed in US 2012/0143400 A1 comprises a head-mounted wireless transmitter, a microcomputer, as well as accelerometer and gyroscope microsensors adapted for measuring the angular position of the head both in the vertical and horizontal directions. According to the method described in the specification the tilt angle of the head is in straight proportion to the speed of the wheelchair, and the tilt direction of the head is the same as the direction of travel of the wheelchair. This method has the same disadvantages as the control method according to WO 2007/082969 A1, and it also does not allow alternative relationships for describing the input and output signals.

In a system according to US 2012/0310470 A1 control information is received and diagnostic data are sent by a control unit of a wheelchair over a short-range wireless connection, where the short- and long-range wireless transmitter may also be a smartphone or a tablet computer. The disadvantages of this solution are that a smartphone or tablet computer can be connected to the wheelchair exclusively using a wireless connection, which is less safe than wired connections, and that the embedded sensors of the smartphone or the tablet computer are not utilised for controlling the vehicle.

According to US 2008/0135321 A1 at least one sensor adapted for detecting the tilt angle of the vehicle is mounted on an electric personal vehicle, and falling over or getting stuck of the vehicle is automatically signalled by means of the sensor. It has the disadvantage that the sensor signals are not utilised for controlling the vehicle.

The solution disclosed in US 2013/0253769 A1 prevents the directional drift of the wheelchair by monitoring the angular velocity of the wheels applying optical or magnetic sensors and compensating it as a function of the input signal. It has the disadvantage that most wheelchairs lack the encoder. Also, sensors and transmitters disposed on or near the wheels are subject to contamination and physical damage.

U.S. Pat. No. 5,555,495 describes a so-called 'man in the loop' method, in which a human user is considered as a disturbance variable in the human-machine system. Adaptivity is implemented by modelling, which is disadvantageous because it has a slow learning curve, and also does not develop the skills and abilities of the user (which is of utmost importance for a wheelchair person). It is resource-demanding, and may learn only from commands already executed, which is not adequate in certain cases.

DISCLOSURE OF THE INVENTION

The object of the invention is to eliminate the drawbacks of known solutions and thereby provide a personal vehicle and a control apparatus and control method for the vehicle that allows for safe, customisable driving control. A further objective is to provide a control that is capable of filtering and automatically compensating the noises resulting from the surface unevenness of the road, and from downward and upward slopes, thereby improving ride stability.

The above objects are achieved by the control apparatus according to claim 1, the personal vehicle according to claim 7, and the method according to claim 9. Preferred embodiments of the invention are defined in the dependent claims.

BRIEF DESCRIPTION OF THE DRAWINGS

Preferred embodiments of the invention are described below by way of example with reference to the following drawings, where FIG. 6 is an illustration of three levels of customisation, FIG. 7 schematically illustrates possible inputs of the platform, FIG. 8 schematically illustrates the application of two different types of input devices, FIG. 9 schematically illustrates measures taken for stability control.

MODES FOR CARRYING OUT THE INVENTION

Figure 1:
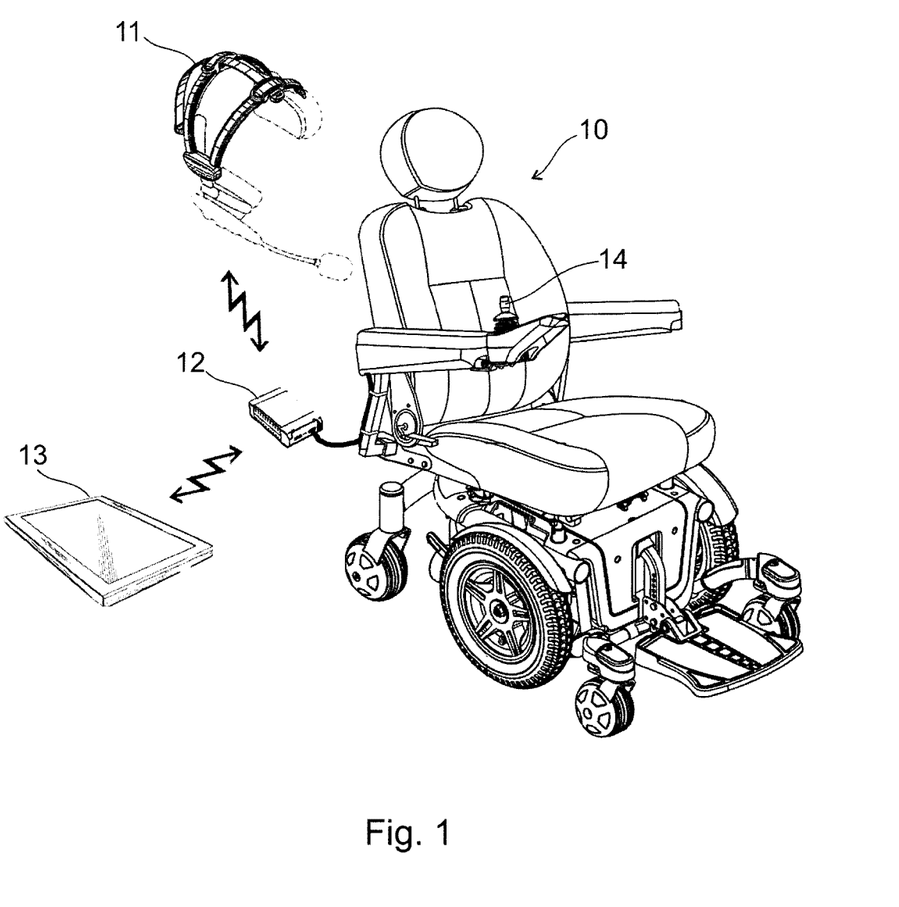
FIG. 1 is a schematic spatial drawing of an exemplary electric wheelchair provided with the control apparatus according to the invention.

In FIG. 1 a schematic spatial drawing of an exemplary electric wheelchair 10 provided with a control apparatus according to the invention is shown. The invention may of course be applied in conjunction with other personal vehicles, but the wheelchair-embodiment is described in more detail herebelow.

In the illustrated preferred embodiment the wheelchair 10 may be controlled, in addition to applying a conventional joystick 14, by means of so-called body-mounted inertial sensors and motion sensors. According to the invention, at least two motion sensing units and a processing unit are applied in the following arrangement: a first motion sensing unit 11 is mounted on a freely movable body part of the driver, and a second motion sensing unit 12 is secured to the wheelchair 10, i.e. to the personal vehicle. Both motion sensing units use the environment as a reference base, in which the vehicle and the driver are present. In a preferred embodiment, the reference base, i.e. the common frame of reference is defined by the direction of gravity and by the magnetic direction (e.g. the magnetic North). As far as the orientation is concerned, two directions provide an unambiguous frame of reference in space, wherein the orientations can be determined by means of two motion sensing units 11, 12. The orientations of the two motion sensing units 11, 12 are continuously changing by the motion of the units. In the context of the present application the term 'motion sensing unit' is used to refer to all units which are capable of determining tilt and turn (in the following: orientation) values relative to an external frame of reference. As it is described below, the orientation relations between the vehicle and the driver are calculated by the processing unit utilising fused signals of the two motion sensing units 11, 12, which orientation relations are then applied by the processing unit for vehicle control.

In a preferred embodiment of the electric wheelchair control platform, controllable also with inertial sensors, the motion sensors may be any electronic devices that are capable of 3-axis orientation detection. The orientation sensor to be mounted on the user can be secured universally to any part of the body. In the illustrated preferred embodiment a head-mountable first motion sensing unit 11 is shown. As illustrated din FIG. 1, the electronics of the platform has wireless connection to a tablet computer and to the inertial headset.

According to the invention the first and second motion sensing units 11, 12 are adapted for determining orientation with respect to the same external frame of reference. Based on a first orientation supplied by the first motion sensing unit 11 and on a second orientation supplied by the second motion sensing unit 12 a so-called inertial control signal is generated and outputted by a processing unit 13 as a function of a relative orientation of the first motion sensing unit 11 and the second motion sensing unit 12. In a preferred embodiment of the invention the processing unit is implemented as a PC, a tablet computer, a smartphone, or a game console.

The control apparatus according to the invention preferably observes trends in variations of input parameters and compares patterns. It is also capable of learning and recognising gestures that may be assigned to arbitrarily chosen functions. In an 'intelligent' embodiment the control apparatus is capable of learning gestures and driving habits, and is thereby capable of adaptation both to the environment and to the driver of the vehicle.

In a more preferred embodiment, the control apparatus is also capable of remote surveillance of the personal vehicle. It is preferred, furthermore, if the user, by means of the control apparatus, may control a computer, a smartphone, or a tablet computer, or may give signal to electronic switches operating lights, doors, lifts and other electronic appliances.

The control signal generated from the difference between the orientation of the body part moved by user and the orientation of the wheelchair 10, or, in other words, the relative orientation thereof has been termed 'inertial control signal'. The reason for incorporating the first motion sensing unit 11 in a head-mounted unit (headset) in the present preferred embodiment is that the invention was developed primarily for people paralysed below the neck.

Figure 2:
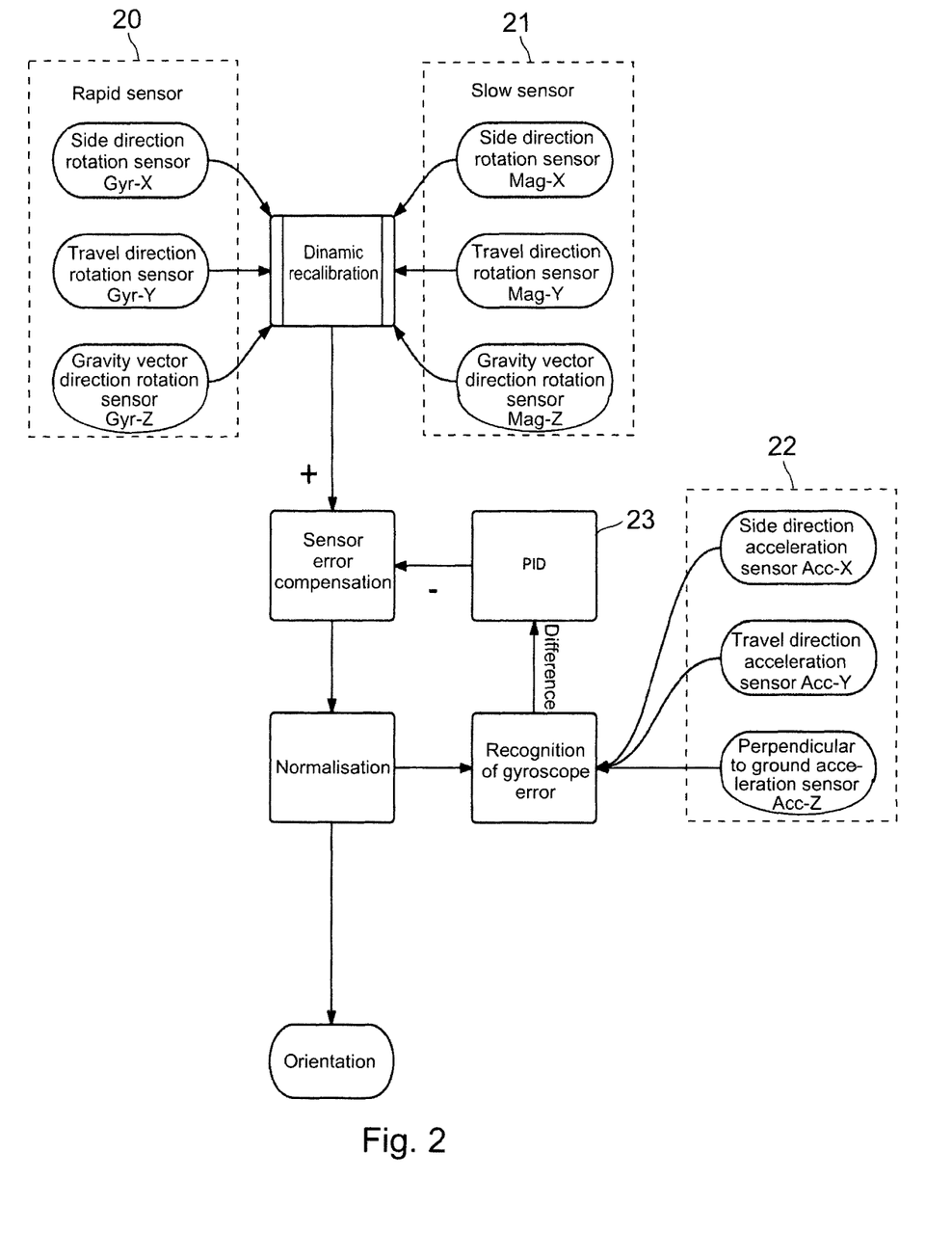
FIG. 2 is a schematic block diagram of the exemplary motion sensing units utilised in the invention.

The external frame of reference (reference base) is therefore preferably a coordinate system defined by the magnetic field and gravitational field of the Earth. In case of using such a reference, commercially available sensors, e.g. magnetometers (comparison relative to the Earth's magnetic field) and accelerometers (comparison relative to gravitational field) can be applied advantageously. In FIG. 2 the structure of the identically structured first motion sensing unit 11 and second motion sensing unit 12 is illustrated. Each of the units comprises a quick-reaction triple-axis gyroscope rotation sensor 20, a slow-reaction triple-axis magnetometer rotation sensor 21 adapted for recalibrating the signal of the gyroscope rotation sensor 20 time to time, and a triple-axis accelerometer 22 adapted for compensating a drift of the gyroscope rotation sensor 20. These sensors preferably consist of one-dimensional sensor components oriented in the direction of the three (reference frame) axes. It is clear that the same sensors may be applied also for detecting the directions defining the external frame of reference, which simplifies the configuration.

So-called 'sensor fusion' is applied in the inventive solution in a twofold sense. Firstly, during inertial control the control of the wheelchair is realised by means of the relative orientation (with respect to each other) of the two—preferably identically structured—motion sensing units. Secondly, ride stability of the wheelchair 10 is ensured by the motion sensors arranged in the control apparatus itself. As it is described below, drift is compensated by the invention based on gravity and geomagnetism.

Due to their vibrating operation, the microelectromechanical gyroscopes (best suited for measuring rapid rotation) comprised in the triple-axis gyroscope rotation sensor 20 are characteristically affected by the phenomenon of 'drift'. A so-called gyroscope drift corresponds to the case when the output of the sensor is non-zero in rest state. This unwanted effect—false rotation sensed without simultaneous acceleration—is recognised by the help of the extremely reliable accelerometers comprised in the triple-axis accelerometer 22, and is compensated by means of a feedback loop shown in FIG. 2 of a PID controller 23 being controlled by the difference value. For sensor error compensation and for recognising gyroscope errors the signals are normalised.

The solution involving gyroscopes and compensated by means of accelerometers is made more stable by orders of magnitude utilising the signals of magnetometers (which react slowly but are free from drift errors) for periodical (i.e. dynamic) recalibration of the gyroscope sensors according to the angular position supplied by the magnetometers. The time difference between recalibrations may be chosen e.g. in an empirical manner, taking into account the given applications. Without recalibration the measurement errors of the sensors would accumulate in the sensor fusion, resulting in the slow rotation (drift) of the direction vector. The compensation process therefore includes fusing the data of the slow-reaction magnetometer and the quick-reaction gyroscope. The raw data of the gyroscope and of the magnetometer are corrected in proportion to the—motion-independent—drift value appearing on the fused output of the three sensors. In extreme cases the gyroscope may become oversaturated (get stuck), when—if no acceleration is present other than gravity—the processing electronics of the gyroscope should be restarted after the magnetometer has been set to the direction. Therefore, the static rotation (i.e. rotation in the absence of acceleration other than gravity) of the direction vector obtained from the fused sensors is measured during operation, and raw data are compensated in proportion to the error value.

The above method is carried out on the signals of the three different sensors for all axes representing the spatial dimensions, the vectors are added, and the orientation thus obtained is handled preferably in a quaternion representation.

In addition to the triple-axis accelerometer 22, to the triple-axis gyroscope rotation sensor 20, and to the triple-axis magnetometer rotation sensor 21—as well as to the microprocessor and radio transmitter—two further sensors may be arranged in the first motion sensing unit 11. In a manner shown in FIG. 3, a pressure sensor 30, allowing the user to send a mode change request to the controller, may be arranged in the rear portion of the headband, and an infrared distance sensor 31 adapted for detecting blinking of the wearer of the headband can also be arranged.

Figure 3:
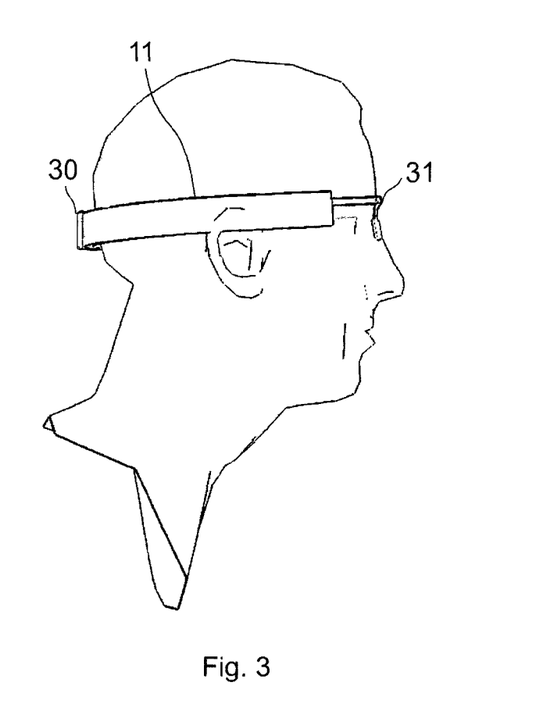
FIG. 3 is a schematic drawing of a headset that may be utilised in the invention, FIG. 4 schematically illustrates the head gestures for control, FIG. 5 schematically illustrates interconnections of an exemplary control apparatus implemented as a hardware-software platform.

When a sudden change is detected in the pressure between the headband and the headrest of the wheelchair 10—i.e. it is detected that the user's head is tilted back—the operating mode of the wheelchair controller is changed by the pressure sensor 30. The two major functionalities of the pressure sensor are controlling the wheelchair 10 itself, and controlling the user interface of the wheelchair by moving the head. Through the user interface, communications and environment-control functions may also be accessed. Pushing the pressure sensor 30 during driving may e.g. stop the wheelchair automatically, or may activate the user interface.

The distance sensor 31 disposed near the user's eye makes use of the physical characteristics of the human eye, namely the vitreous body absorbs light, the eyelids reflect it, and thereby different values can be measured in the opened and closed position of the eye. The frequency of vegetative blinking shows a correlation with the vigilance of the user, but even more importantly it may be used as an 'input device' complementing the conventional mouse, with different functions being assigned to different blink durations. A blink having a duration between e.g. 500 ms and 1 s may correspond to pressing the left mouse button.

Because the fusion of sensor data is realized for the motion detector disposed in the headset in the same manner as for the sensors mounted on the wheelchair, from the difference between them a signal applicable for control purposes may be advantageously generated. For the numeric representation of each vector four floating point values are required: the angles in each of the three spatial planes between the gravity vector used as a reference and the vector to be represented (the angle pairs corresponding to the current plane of rotation), and the rotation angle of the vector (about its own axis) relative to the magnetic North as a reference. During the first start-up of the control apparatus, the orientation of the wheelchair measured relative to the reference directions (gravity, magnetic North) is associated with the direction of travel of the wheelchair, which direction will be applied as a reference for the control signal.

Since the user puts on and takes off the headset every day, after the wheelchair has been powered up, the orientation of the headset relative to the external reference is associated with the forward facing state. After that, in a manner similar to joystick-type input devices, only the angular differences relative to the wheelchair 10 as a reference have to be handled.

Figure 4:
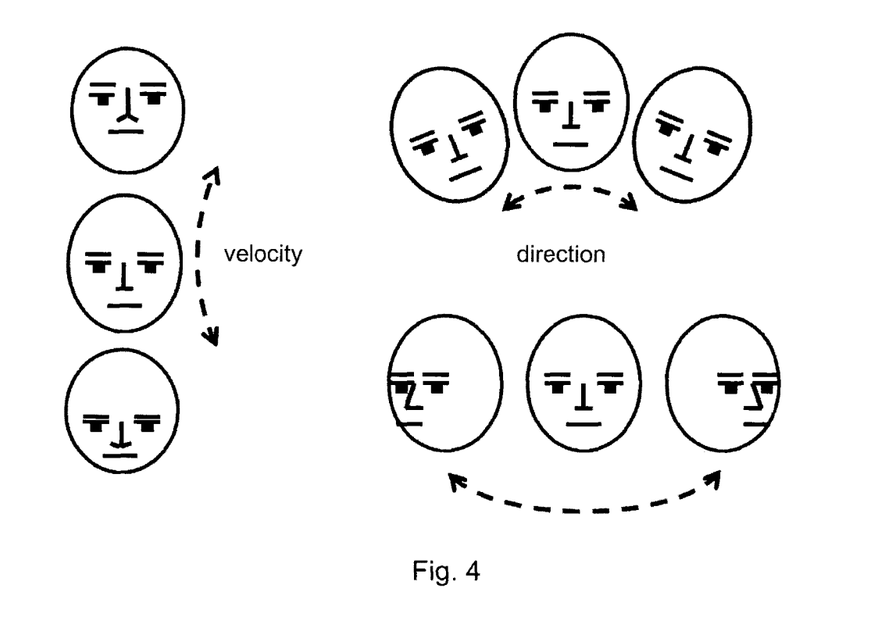

According to the default settings, the proportional adjustment of vehicle speed may be performed preferably by tilting the head backward/forward, as shown in the left part of in FIG. 4. In the default situation illustrated in the right part of the figure, turning (cornering) is preferably achieved by tilting or rotating the head to the left or to the right. The default settings may of course be modified if desired so by the user.

Figure 5:
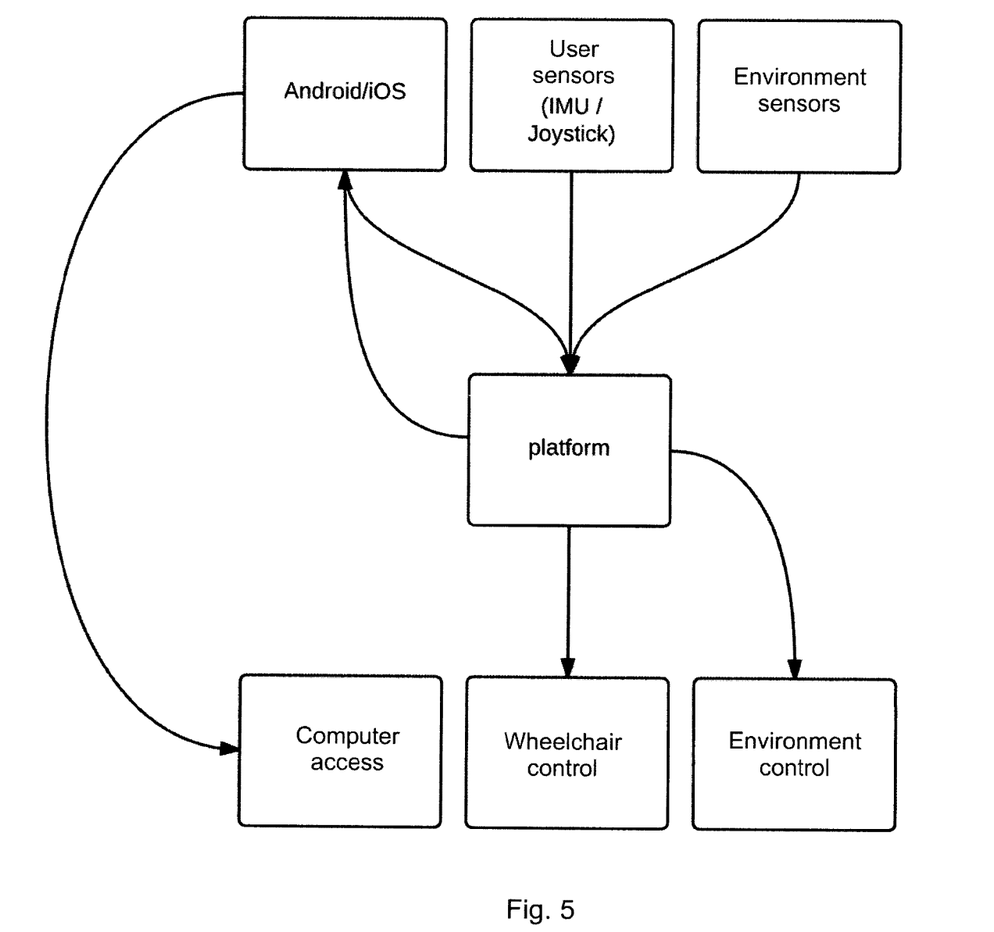

The primary functionality of the control apparatus—which is implemented as a hardware-software platform in the embodiment shown in FIG. 5—is providing safe control and driving of the wheelchair 10, including the filtering and normalisation of control signals, associating the signals with predetermined actuator functions, as well as providing ride stability. It is especially important to filter external noises caused by the unevenness of road surface, and to compensate the drift occurring during turning and straight-line driving.

In addition to driving control by means of a joystick and inertial measurement units (IMU), the control apparatus may support other special, secondary modes of control, such as by taking into account alternatively controllable inputs. Additional sensors applicable for control may be for example distance sensors, stretch sensors, strain gauges, touch panels, mice, position sensors or stereoscopic cameras. Through specialised control functionalities made possible by environmental sensors, automated obstacle avoidance may also become feasible.

Additionally, the control apparatus may provide wireless connection to a computer, or mobile devices which may be operated by the user by the gestures applied for controlling the wheelchair. System configuration may also be performed via a wireless connection using a tablet computer or a smartphone, which may be applied also as a display and communications device.

Furthermore, the control apparatus may issue control orders to door-openers, light switches, electronic devices, and thereby may perform environment control and command functions. No product currently in the market provides all of the above functionalities.

The platform is preferably divided into three well separable layers, wherein the 'lowest' execution layer is constituted by the power electronics unit and its microprocessor, in other words, the power module that is directly responsible for driving the motors and brakes.

The next layer logically above is the so-called 'low-level layer' to which the different input devices communicating by different protocols are connected. This layer comprises the 3×3-axis motion sensor, radio and infrared transmitters and receivers, and the microprocessor performing signal filtering and calculating the control signal. To provide for safe operation, all of the basic control functionalities of the wheelchair are implemented in this layer.

In the uppermost layer, which is constituted by a user interface, there is preferably included a smart mobile device with its embedded GSM, GPRS, and GPS modules, touchscreen, camera, sound processing and speaker devices. This device may be utilised for the configuration of the whole platform, but it is not indispensable for the operation thereof. The settings available in the interactive user interface range from motor power limiting through the diameter of the wheels, personal physical parameters (weight, height), and motion ranges to filter selection and tuning. In addition to that, since the low-level layer allows for monitoring the stable operation of the mobile device, the platform also allows for running—on a large-performance device—self-learning algorithms, modelling systems, gesture recognition applications or software capable of intelligent navigation. As soon as the low-level layer detects that the reaction time of the smart device has increased (for example a noACK or timeout signal is received), the top layer gets prohibited from intervening in vehicle control. However, all such control-related parameters that have improved the safety of driving conditions are stored by the low-level layer, providing appropriate control even in the absence of the smart device.

The universality of the control apparatus is provided primarily by its customisation capabilities. In wheelchair control it is of utmost importance that the control system provides the highest possible level of safety in correspondence with the driver's abilities.

Figure 6:
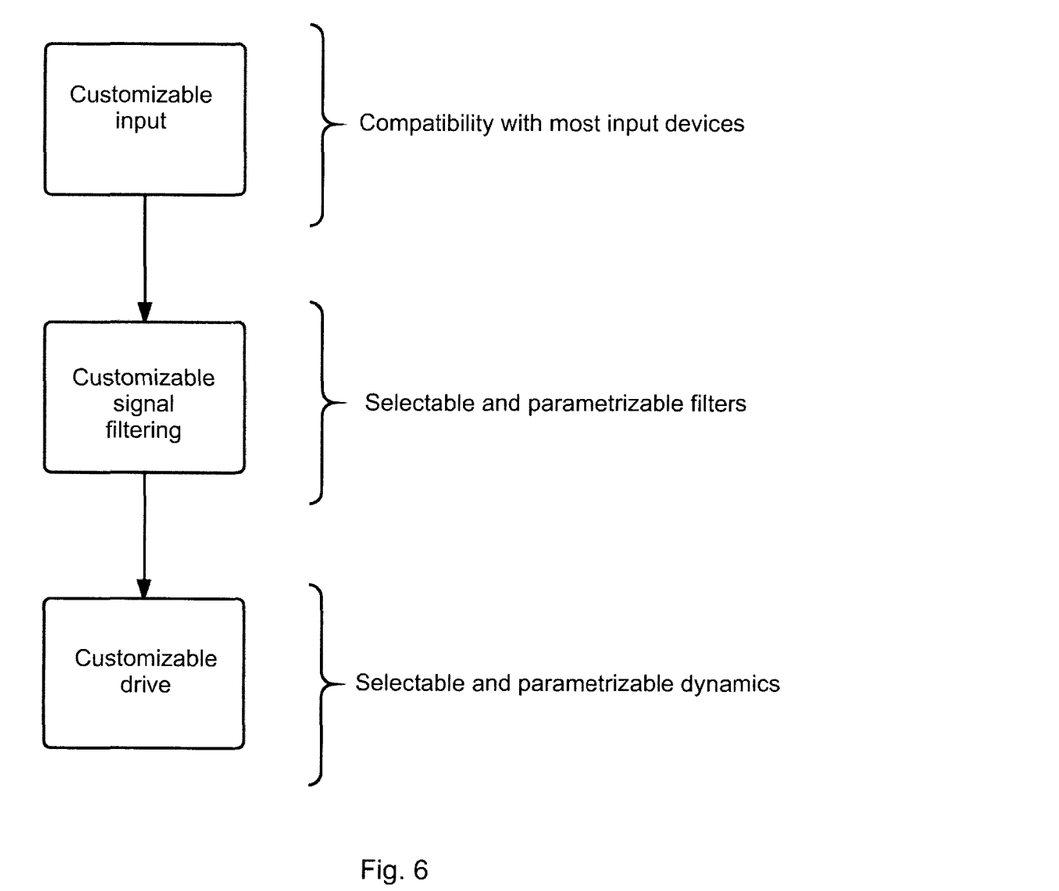

FIG. 6 illustrates the three levels of customisation. The lowest level, the customisable drive means that within the protection limits of the motors (overcurrent protection) the rate of acceleration, the rate of the so-called 'ramps' may be formed by the user conforming to his or her own needs. Currently there is no commercially available device which would allow the owner of the wheelchair to make such changes. The system preferably allows for multiple pre-programmed 'behaviours', from which the user may choose the one best suited for driving conditions, such as low power consumption—high range, or quick maneuvering.

The component shown in the middle of the drawing, i.e. the customisable signal filtering component, is applied for removing with high-efficiency from the control muscle-jerks, tremors occurring from time to time, as well as the uncertainties caused by fatigue due to muscular weakness and spasms. Software filters—based on clinical testing—are preferably selected according to the different types of problems. The parameters of the simplest low-pass, high-pass, windowed, linear or recursive methods are set by the controller in an adaptive manner, and thereby it is also capable of filtering long-term disturbances (such as those resulting from muscle fatigue).

Customisable inputs denote compatibility with a number of input devices and the configurability of such devices. In the primary embodiment of the controller the device is a 3×3=9-axis motion sensor mounted to a body part. However, for disabled persons capable of moving their limbs driving their wheelchair should be an activity connected to simultaneously developing their healthy body parts. Thereby the control apparatus may be factory-integrated with other types of input devices in addition to the above disclosed devices, for example optical or capacitive joysticks or touch panels. The control apparatus may comprise a number of standard connection interfaces (for example USB, BT, WIFI, IRDA).

Figure 7:
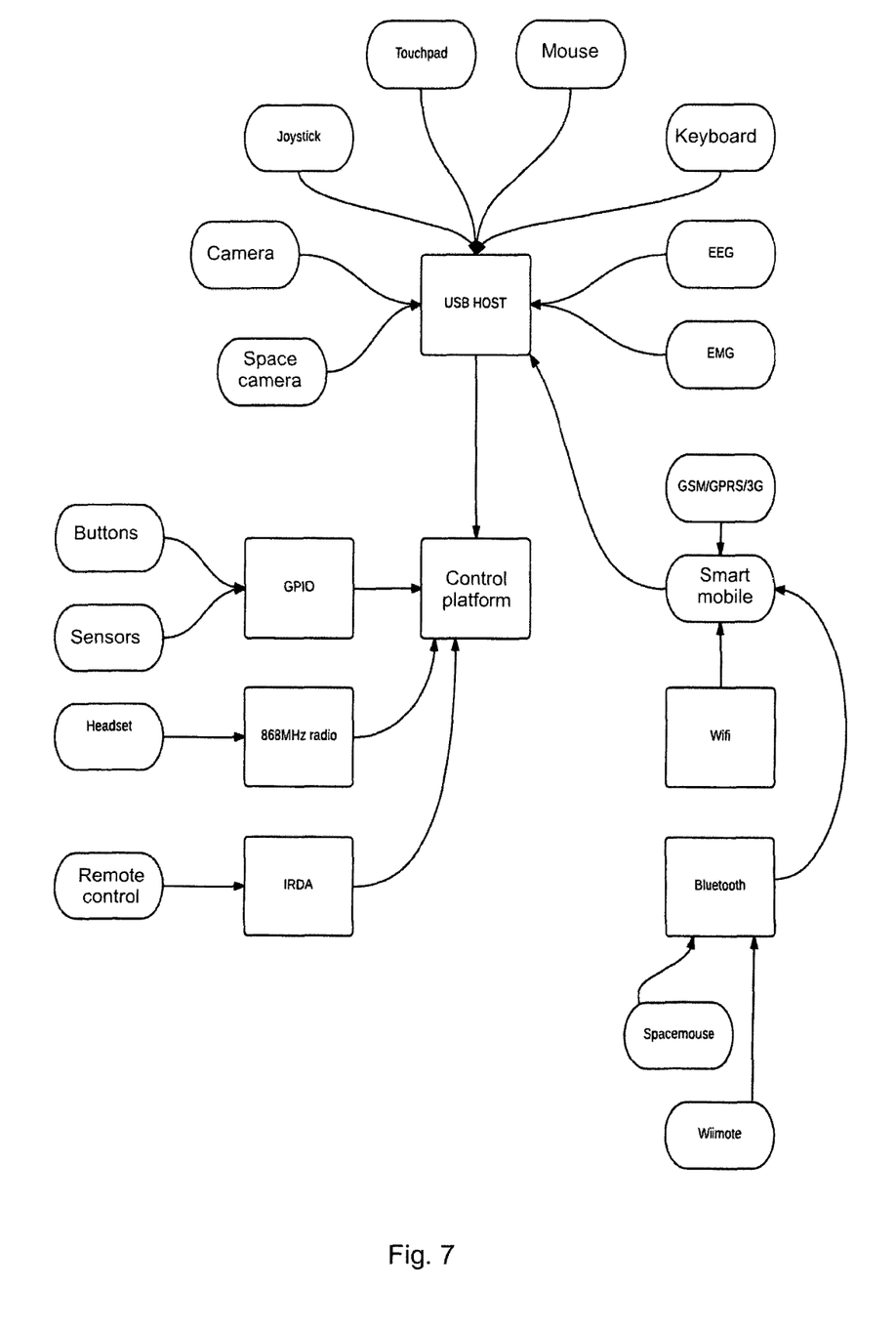

In a manner illustrated in FIG. 7 the platform may comprise several inputs on both the microprocessor unit and the smart mobile device. Since each person has a different ability profile, the most appropriate input device should be provided for everybody for driving the wheelchair 10. In extreme cases a tetraplegic user (all four limbs affected by paralysis) may control the wheelchair by simple head movements and making spatial gestures with the head. The physiological causes of diplegia may include several medical conditions. Persons suffering from chronic muscular dystrophy, who gradually lose their muscle strength, can only use special, very high-sensitivity input devices such as capacitive touch panels or optical joysticks. By the above described arrangement of the platform, compatibility with the highest number of commercially available devices was intended. Patients with neurological conditions affecting systems other than the movement system (e.g. cognitive, visual) can be provided with navigation aids applying the optionally connected environmental sensors.

Figure 8:
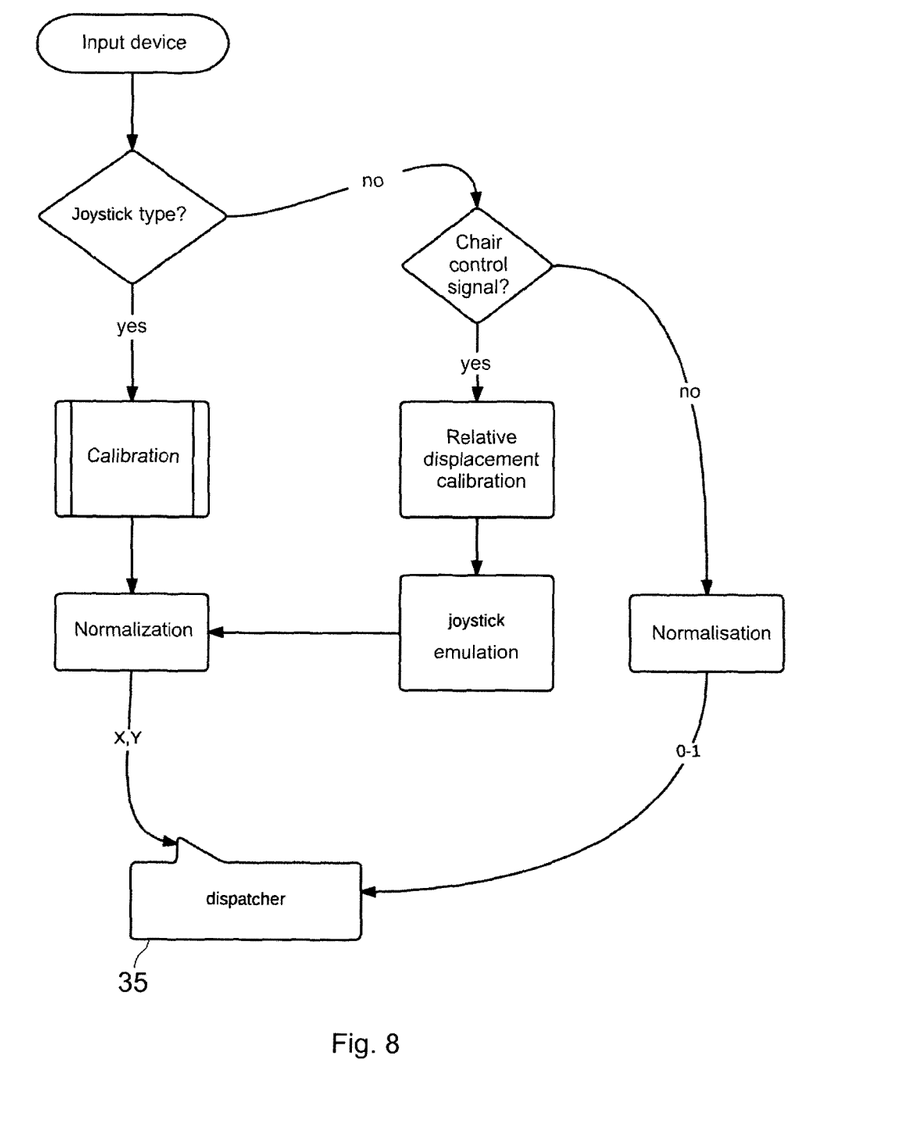

According to the sequence of steps illustrated in FIG. 8, basically two different types of input devices may be applied for the control apparatus: joystick-type devices (measuring absolute displacement) and mouse-type (measuring relative displacement).

In case of the former, after measuring the peak values (calibration) the signal is fit into the range compatible with the system (normalisation), and then it is fed to the so-called dispatcher module 35, a software module adapted for associating the input signals with the outputs corresponding to the configuration.

Mouse-type devices supply information on relative displacement, and thus peak values are associated with the rate of change, and are then applied for modelling the physical operation of a joystick (physical characteristics of the model, such as the spring force, can be calibrated). For example, a touchpad or a finger swipe over a sensor panel provides a vector starting from an arbitrary origin. In this case, therefore, the calibration of relative displacements is required. As long as the finger is touching the sensor surface, the Cartesian components characteristic of a physical joystick are passed on by a software module adapted for joystick modelling and emulation, which are then fed to the dispatcher module 35 after normalisation. However, as soon as the finger is lifted from the sensor surface, the virtual stick is returned to the centre position by the joystick emulator utilising physical models of the springs.

In addition to the above mentioned two signal types, further signals—for example, signals coming from switches and environmental sensors—are also present which are not necessarily related directly to the control of the wheelchair (e.g. horn). These are passed on to the dispatcher module 35 after normalisation.

Figure 9:
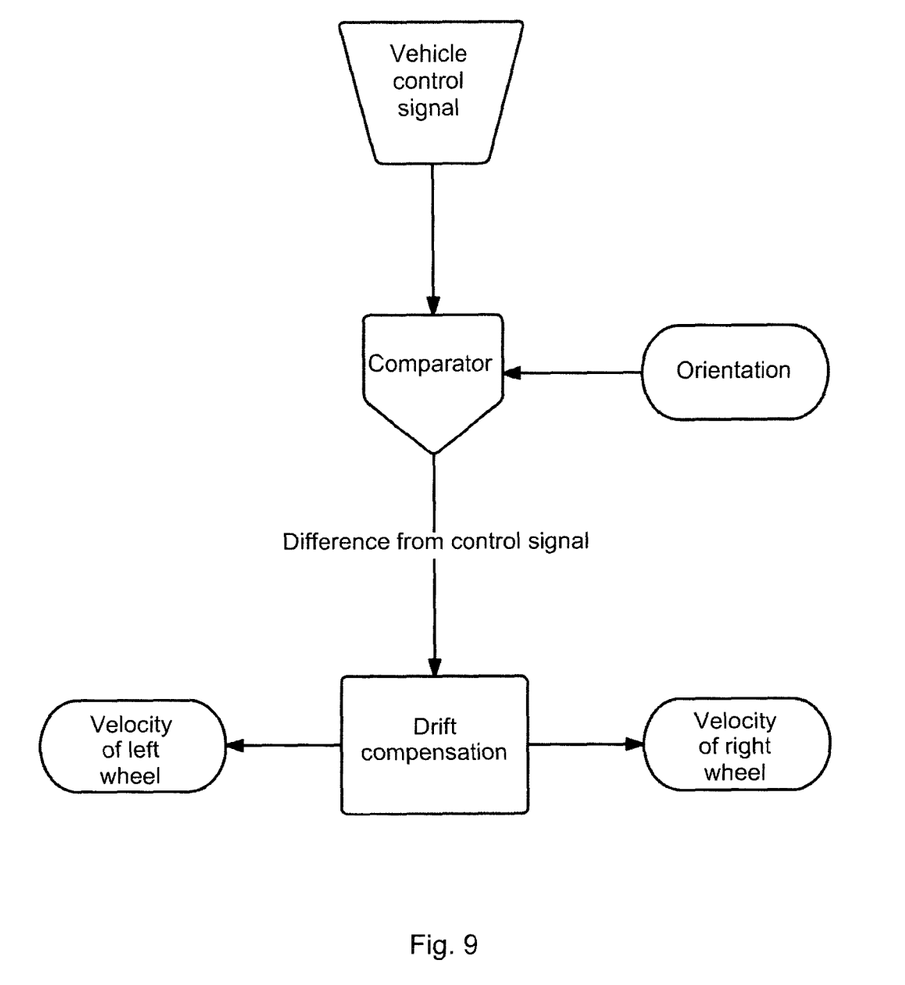

FIG. 9 schematically illustrates the measures taken for stability control. The 'drift' of the personal vehicle is the phenomenon of diverging from the direction of travel set by the user. This may result from the surface unevenness of the road, from the difference between the grip of the left and right-side driven wheels or between the distance travelled by them (for example on a hillside), or from the non-uniform performance of the driving motors and differences caused by mechanical wear.

To compensate the drift of the vehicle, PID control known per se may be applied, with the process variable being the fused data of the inertial sensors of the platform—the orientation of the vehicle—and the controlled variable being the control signal of the vehicle. The software component of the PID controller calculates the difference between the control signal and the orientation of the vehicle (which will be the error determined by the comparator), and tends to minimise it. According to the default settings, the feedback loop (not shown) is pre-tuned (on the basis of experiments), but the reaction time is being modified in an adaptive manner corresponding to the error/difference value, by adjusting the constants of the proportional, integral and derivative parameters (used as fine-tuning parameters) within narrow, experimentally established ranges. In case of higher difference values a more aggressive intervention is made by the system in order to minimise the error, while to smaller error values it responds with smaller-scale correction interventions. The intervention is performed by a drift compensation unit which, in case of a wheelchair, adjusts the velocity of the left and right wheels by an appropriate amount. The present solution significantly improves ride stability in the above mentioned problematic cases, i.e. not only during straight-line motion.

Figure 10A:
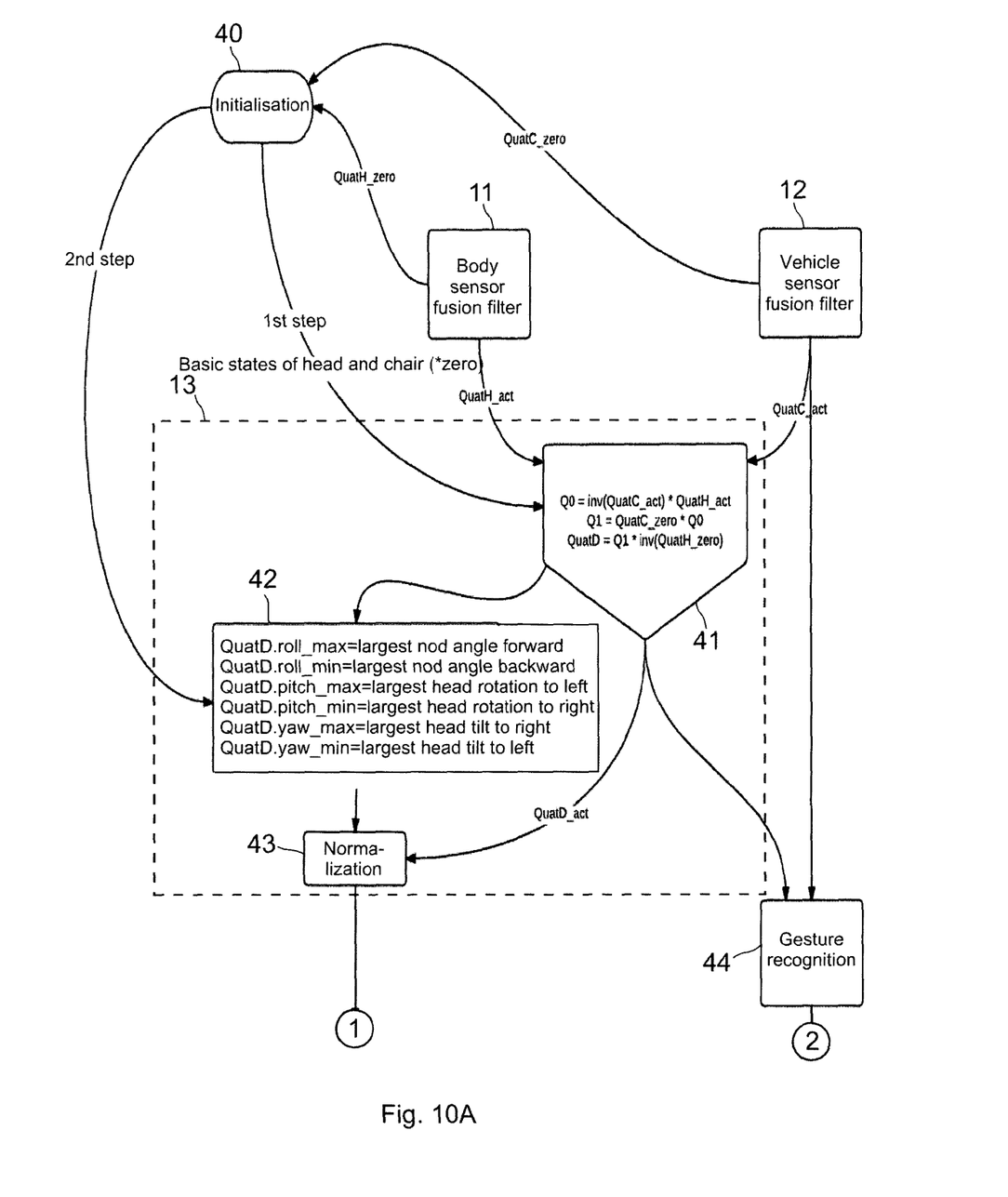
FIGS. 10A and 10B show a schematic view of a structure of a preferred control apparatus according to the invention, and also the operation of the control apparatus.
Figure 10B:
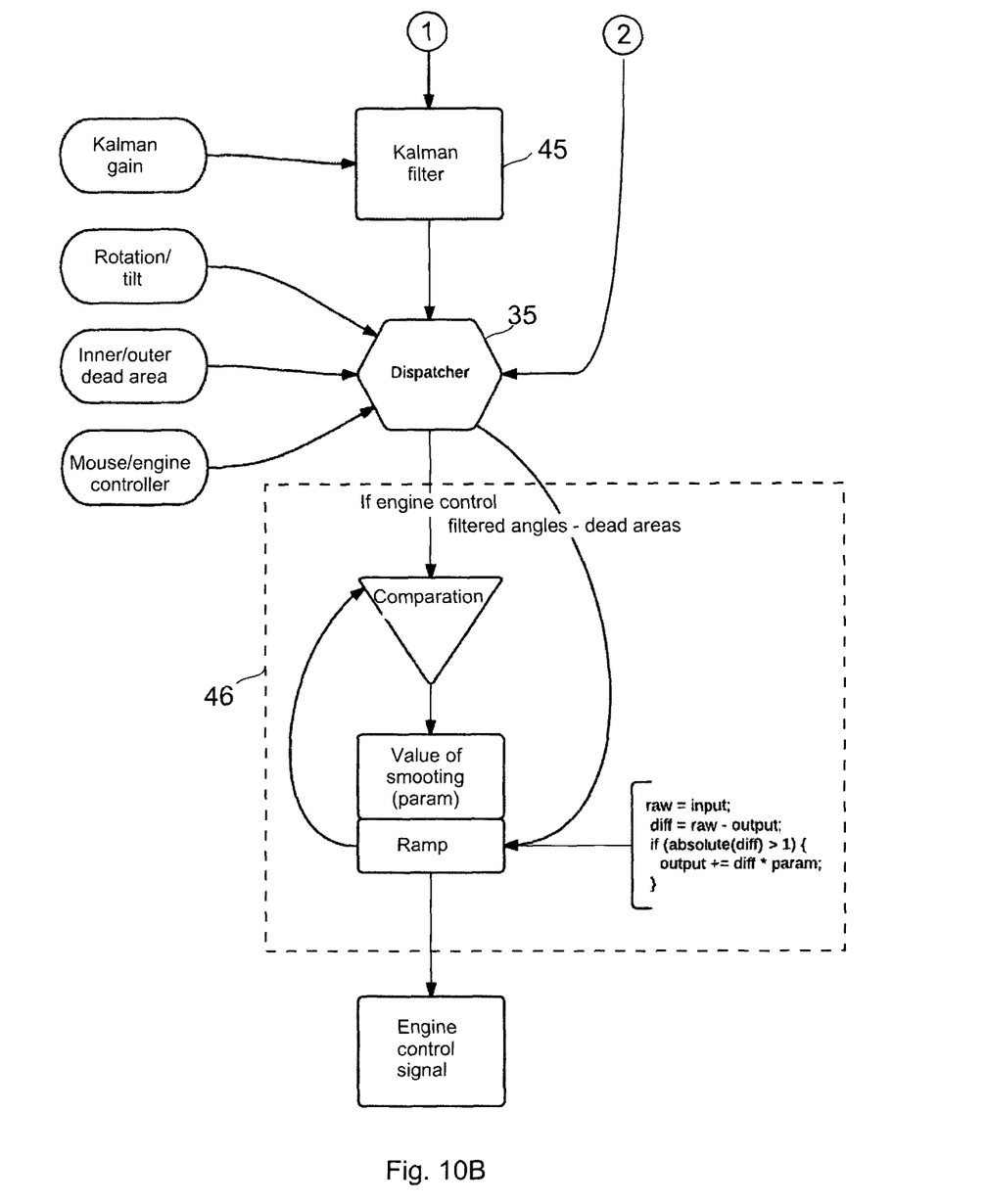

FIGS. 10A and 10B illustrate certain (preferably software-implemented) modules of a preferred embodiment of the control apparatus according to the invention, and also show the flowchart of operation of the control apparatus.

By means of an initialisation module 40 of the control apparatus the wheelchair 10 is configured by user interventions, preferably before operation is started. As a first step, the motion sensing units 11, 12 structured according to FIG. 2, or more precisely, the orientation values thereof, are taken to a basic state with respect to the common frame of reference. As a second step, the peak values characteristic of the user are entered into a peak value module 42. In order to do that, the user has to tilt the head well forward and backward, and rotate it to the left and to the right.

In addition to the peak value module 42 the processing unit 13 further comprises a quaternion vector calculation module 41 adapted for calculating relative orientation preferably applying the formulas shown in FIG. 10A. A normalised orientation value is obtained at the output of a normalisation module 43. For the subtraction operation, i.e. for freeing the signal of the body-mounted sensor of the external noises to which the wheelchair 10 is subjected, a quaternion-based calculation method is preferred for calculating the relative orientation, whereby matrix operations become unnecessary. As a result of the subtraction operation the control signal issued by the user relative to the wheelchair 10 is obtained.

The preferred embodiment illustrated in FIG. 10A further comprises a gesture recognition module 44 that is preferably implemented on a smartphone and uses a neural network. The gesture recognition functionality allows for entering additional commands, for example for entering a constant target speed for the wheelchair 10, for setting velocity levels, or for halting the wheelchair instantly. By means of the recognition of predetermined gestures or gestures learned by the control apparatus, the commands associated with the specific gestures are executed instead of generating a control signal from the signals of the motion sensing units 11, 12 as described above. A preferred embodiment comprises a gesture recognition module 44 adapted for recognising gestures performed utilising the first motion sensing unit 11, and, in case a predetermined gesture is recognised, the dispatcher module 35 issues a control signal corresponding to the command assigned to the gesture instead of issuing the inertial control signal. Thereby, the gestures are separable from the control signal.

Smartphones with higher computing capacity are capable of applying a variable window-size sampling technique for recognising the movements of the headset, i.e. the temporal change of the orientation of the head. To achieve that, spatial envelope surfaces are generated that may be tested quickly and efficiently using their local characteristics, and may be recognised consistently within the allowed deviation.

Utilising applications implemented for smartphones the involuntary high-amplitude convulsions of the driver and the tremors occurring from time to time may be filtered also by gesture recognition. The dynamics of maneuvering may be learned simultaneously by the driver and the vehicle. The self learning application may be manually switched into an intensive learning mode wherein the gesture recognition module 44 memorises the spatial envelope of a sequence of movements. According to what has been described above, these movement patterns may be interpreted as commands, and may be associated with arbitrary functions, such as: emergency stop, answer/reject call, start external applications. If, for example, the sensor is displaced, the resulting change can be indicated to the control apparatus—for example by gesture control or applying the pressure sensor 30 disposed in the headset—, which then calculates the deviation and the compensated vehicle control signal. In case the first motion sensing unit 11 falls off or the vehicle falls over, the control of the vehicle may be blocked automatically, and an emergency call may be made.

As illustrated in FIG. 10B, the main branch of the flowchart comprises the step of feeding the inertial control signal generated from the normalized differential signal (the relative orientation) in a Kalman filter 45, which performs predictive comparison of the current control signal value with the previous value in a known manner, thereby filtering out unrealistically large changes resulting for example from a convulsion. The Kalman filter 45 is customised i.e. it is tuned to the movement style of the given user preferably by adjusting the Kalman gain in a manner known per se.

Further customisation is performed by parametrising the dispatcher module 35 adapted for receiving the filtered inertial control signal. The dispatcher module 35 receives as an input whether the user controls the wheelchair by tilting or rotating the head. Preferably, an internal and an external dead area are also specified. The internal dead area serves for preventing the wheelchair 10 from moving in a 'jumpy' way, as small head movements will not cause the chair to start. The external dead area is chosen taking into account the 'normal' amplitude of body movements, which means that a rotation or tiling of the head having an amplitude falling into the external dead area does not normally occur. Therefore, a signal in the external dead area may for example indicate that the user has become unconscious. The dispatcher module 35 therefore only affects the motion of the personal vehicle in case the filtered inertial control signal is outside the dead area(s).

By toggling an input of the dispatcher module 35 the user may switch from using the headset for vehicle control to using it as a mouse with the interconnected tablet computer, and vice versa. The user may switch between the two modes for example by pressing the pressure sensor 30.

A smoothing module 46 that receives the output signal of the dispatcher module 35 preferably consists of components known per se that are shown in the figure, providing that after filtering and applying dead areas the inertial control signal is also smoothed such that it does not include high acceleration values and rapid changes of direction. The actual motor control signal is obtained at the output of the smoothing module 46 performing adaptive ramp smoothing of the signal.

Figure 11:
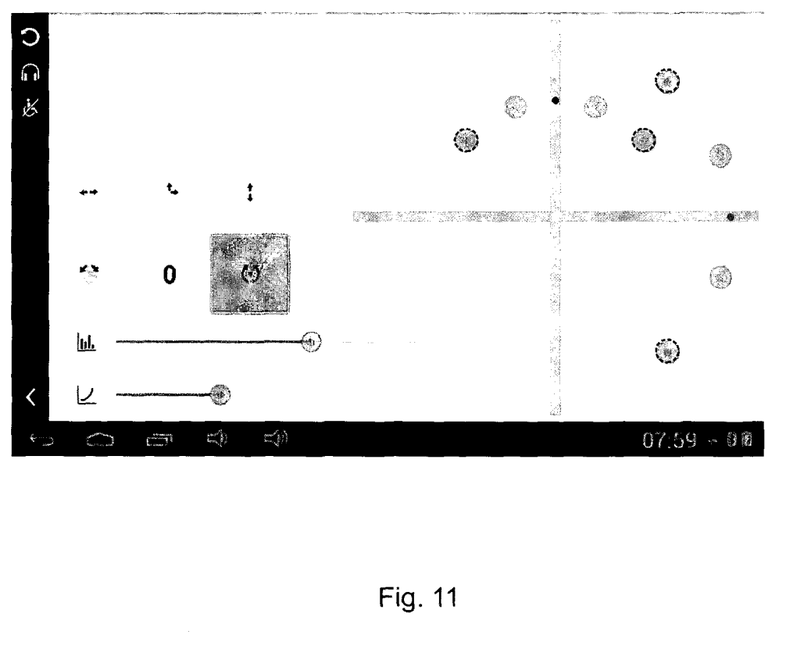
FIG. 11 shows graphics displayed in an exemplary user interface for adjusting the headset and the motion sensing unit connected thereto.

FIG. 11 shows the graphics displayed in the exemplary user interface required for adjusting the headset, more specifically the first motion sensing unit 11 connected thereto. By pressing the buttons indicated by arrows, left and right, forward and rearward, as well as forward/right directions can be exchanged. The first element of the next row of buttons is for turning on and off ride stabilisation provided by the platform, the '0' button is for setting the orientation of the wheelchair relative to the direction of travel, and the square button can be used for calibrating the headset, as well as for selecting between sideways tilting and rotating the head as the control action for turning the wheelchair.

A first slider below the row of buttons serves for setting the initial rate of signal smoothing, while the slider below serves for adjusting the dynamics of the control signal.

The outer concentric circle on the right represents speed, while the inner one indicates the turn. The circles with dashed contours represent the end status, beyond which the user cannot turn or tilt his or her head, while the circles without contours indicate the limits of the neutral zone which may also be interpreted as the dead area of a joystick, meaning that movements within this zone do not affect the motors.

Further characteristics of smartphones may also be put to use by the invention, for instance communication over the Internet, while the body-mounted sensor, i.e. the first motion sensing unit 11 may also be applied for moving a mouse pointer. Similar to other settings, mouse settings can be accessed via the configuration interface. All settings, including the customisation settings of the system, may preferably be made in two ways: applying the touch panel of the mobile device, or by moving a pointer using the body-mounted sensor. For clicking the mouse, the user may choose from four different modes: in the first mode the mouse is automatically clicked once the pointer is kept in a zone of a chosen size for a given time, in the second mode the mouse is activated by sound recognition, for example making a snap with the tongue, saying a word, or making a sound having a given frequency. The third mode involves face recognition, while the most preferred is the fourth mode wherein mouse clicks can be made respectively with the left and right button by blinking with the left or the right eye. Applying the WIFI or Bluetooth connection provided by the smartphone, the mouse functionality may be extended to operate other computers. Using the pointer and the on-screen virtual keyboard, speech-impaired users may enter text to be read out loud by the speech synthesiser module of the software. The speed and voice tone of the synthesised speech may be modified using the same interface.

The control apparatus according to the invention has several advantages over existing solutions. According to the inventive solution, fused sensor data describing the movement of the vehicle and that of the driver are treated as separate inputs. A significant advantage over solutions applying a single sensor unit is that signals disturbing the motion control of the vehicle may be filtered out with high certainty without reducing the reaction time of the vehicle. The unevenness of surface, downward and upward slopes do not influence the control of the vehicle, and the full power of the vehicle over the entire speed range can be utilized. Using the software capable of self-learning it is easy to learn in an intuitive manner how to drive the vehicle, which becomes safer. The use of the system provides countless additional advantages related to internet-based communications, and to the operation of electronic devices and computers.

An important advantage of the invention is that its operation is based on processing the signals of two—preferably identical—sensor systems: one for relating the state of a body part moved by the user to an external frame of reference, and another for relating the state of the vehicle to the same reference frame, and generating the control signal of the vehicle from relatively measured, relative states of these two signals, thereby making the signals of the body-mounted sensor and thus the control signal of the vehicle independent of external sources of noise.

Another significant advantage is that the sensor system may consist of microelectromechanical sensors, namely a 3-axis accelerometer, a 3-axis gyroscope, and a 3-axis magnetometer. Thereby, the sensor units can be applied for determining the angular position and rotation of the object relative to the magnetic field and gravitational field of the Earth. Utilising the magnetometer as a compass, the drift of the gyroscopes may be compensated by means of sensor fusion. Because the applied sensors are extremely reliable, cheap mass-produced products, they are incorporated in most state-of-the-art information technology products, such as smartphones, tablets, and cameras, where they are applied mostly for navigation purposes and for automatic screen rotation.

Therefore, for measuring the position/orientation of the vehicle, the embedded sensors of a tablet computer may be applied, as the tablet computer is also capable of displaying the user and configuration interfaces. In addition to the above, an Internet-enabled device provides a wider range of communications and navigation applications for people paralysed below the neck that may extend their interactions to the fields of videophoning, global positioning, voice search on the Web, on-screen keyboard, and speech synthesis.

A further significant advantage is that, although the measurement of the body part's orientation/position requires a dedicated device consisting of the above listed sensors, a microprocessor responsible for sensor fusion, and a radio transmitter for data transmission, in addition to receiving the signals of the dedicated device the software is capable of receiving signals from other position sensor devices communicating over Bluetooth, WIFI, or USB connection. Thereby, other commercially available devices may also be connected and applied for the purposes of the invention, such as (the embedded sensors of) smartphones, the joysticks of game consoles (e.g. Nintendo WII, Xbox controller), and 3D mice (e.g. SpaceMouse).

Another advantage of the invention is that the vehicle control software may be developed with the use of smartphones in mind. This is important because caretakers of disabled persons often use secondary joysticks for driving wheelchairs when the owner is either—temporarily—not able to drive it, or is not sitting in the wheelchair. Running the wheelchair control application on their mobile phones, caretakers may use their mobile phone as a secondary joystick for driving the wheelchair.

A further advantage is that, due to its modularity, the invention allows for connecting several different joystick- or mouse-type devices, meanwhile retaining the ride stability achieved by inertial sensors. Modularity is manifested in both the hardware and software configuration of the invention, since the software components may also be chosen and customised as required.

The inventive control apparatus or wheelchair control platform operable also by body-mounted inertial sensors allows the signals of the body-mounted sensors worn by the driver, or the signals of the movable input devices to be made independent from external effects, filtering out noises resulting from the unevenness of road surface, thereby providing that vehicle speed is kept constant on upward and downward slopes, compensating for the vehicle's directional drift without user intervention. The digital filters included in the wheelchair controller can be parametrised to suit the needs and capabilities of the user, thereby allowing for controlling the vehicle's motion in an adaptive manner.

The platform according to the invention enables persons in need of controlling a wheelchair to connect different input devices to the control electronics of the wheelchair in order to ensure the safe driving of the vehicle.

The invention is, of course, not limited to the preferred embodiments described in details above, but further modifications, combinations of features and variants are conceivable within the scope of protection determined by the claims.

The invention claimed is:

1. A control apparatus for a personal vehicle, comprising:
a first motion sensing unit that mounts on a body part and determines a first orientation with respect to an external frame of reference,
a second motion sensing unit that mounts on the personal vehicle and determines a second orientation with respect to the external frame of reference, and
a processing unit that outputs an inertial control signal corresponding to a relative orientation of the first motion sensing unit with respect to the second motion sensing unit determined based on the first orientation supplied by the first motion sensing unit and the second orientation supplied by the second motion sensing unit,
wherein the external frame of reference is a coordinate system defined by the magnetic field and the gravitational field of the Earth, and each of the first motion sensing unit and the second motion sensing unit comprises a triple-axis gyroscope rotation sensor, a triple-axis magnetometer rotation sensor used to recalibrate signals of the triple-axis gyroscope rotation sensor, and a triple-axis accelerometer used to correct a drift of the triple-axis gyroscope rotation sensor.

2. A control apparatus for a personal vehicle, comprising:
a first motion sensing unit that mounts on a body part and determines a first orientation with respect to an external frame of reference,
a second motion sensing unit that mounts on the personal vehicle and determines a second orientation with respect to the external frame of reference, and
a processing unit that outputs an inertial control signal corresponding to a relative orientation of the first motion sensing unit with respect to the second motion sensing unit determined based on the first orientation supplied by the first motion sensing unit and the second orientation supplied by the second motion sensing unit,
wherein the processing unit includes one or more software modules comprising:
a Kalman filter that receives the inertial control signal, and
a dispatcher module that receives a filtered inertial control signal as an output of the Kalman filter, and
wherein the dispatcher module includes one or more of an internal dead area and an external dead area, and the dispatcher module only affects the motion of the personal vehicle if the filtered inertial control signal is outside at least one of the one or more dead areas.

3. A control apparatus for a personal vehicle, comprising:
a first motion sensing unit that mounts on a body part and determines a first orientation with respect to an external frame of reference,
a second motion sensing unit that mounts on the personal vehicle and determines a second orientation with respect to the external frame of reference, and
a processing unit that outputs an inertial control signal corresponding to a relative orientation of the first motion sensing unit with respect to the second motion sensing unit determined based on the first orientation supplied by the first motion sensing unit and the second orientation supplied by the second motion sensing unit,
wherein the processing unit includes a software module comprising a gesture recognition module that allows entry of commands assigned to predetermined gestures, and, in case a gesture is recognized, initiates execution of a command corresponding to the recognized gesture, and
wherein the gesture recognition module recognizes gestures performed using signals received from the first motion sensing unit, and the processing unit includes a software module comprising a dispatcher module that issues a control signal corresponding to the command assigned to the gesture instead of issuing the inertial control signal in case a predetermined gesture is recognized.

4. A personal vehicle comprising the control apparatus according to claim 3.

5. The personal vehicle according to claim 4 wherein the personal vehicle is a wheelchair with electric propulsion.

* * * * *